(12) United States Patent
Li et al.

(10) Patent No.: US 11,130,115 B2
(45) Date of Patent: Sep. 28, 2021

(54) SELECTIVE HYDROGENATION CATALYST, PREPARATION METHOD AND APPLICATION THEREOF

(71) Applicants: ZHEJIANG UNIVERSITY, Zhejiang (CN); ZHEJIANG NHU COMPANY LTD., Zhejiang (CN); SHANDONG NHU PHARMACEUTICAL CO., LTD., Shandong (CN)

(72) Inventors: Haoran Li, Zhejiang (CN); Yong Wang, Zhejiang (CN); Baishan Hu, Zhejiang (CN); Xiao Ma, Shandong (CN); Dan Qiu, Zhejiang (CN); Qian Luo, Zhejiang (CN); Zhe Wang, Zhejiang (CN); Shanjun Mao, Zhejiang (CN); Lili Yu, Zhejiang (CN); Qichuan Li, Zhejiang (CN)

(73) Assignees: ZHEJIANG UNIVERSITY, Zhejiang (CN); ZHEJIANG NHU COMPANY LTD., Zhejiang (CN); SHANDONG NHU PHARMACEUTICAL CO., LTD., Shandong (CN)

( * ) Notice: Subject to any disclaimer, the term of this patent is extended or adjusted under 35 U.S.C. 154(b) by 0 days.

(21) Appl. No.: 16/919,097

(22) Filed: Jul. 1, 2020

(65) Prior Publication Data
US 2021/0252484 A1    Aug. 19, 2021

Related U.S. Application Data

(63) Continuation of application No. PCT/CN2020/081041, filed on Mar. 25, 2020.

(30) Foreign Application Priority Data

Feb. 19, 2020 (CN) .......................... 202010102438.6

(51) Int. Cl.
*B01J 31/22* (2006.01)
*B01J 23/44* (2006.01)
*B01J 31/18* (2006.01)
*B01J 31/02* (2006.01)
*C07C 29/157* (2006.01)
*B01J 37/02* (2006.01)

(52) U.S. Cl.
CPC ........... *B01J 23/44* (2013.01); *B01J 31/0217* (2013.01); *B01J 31/0238* (2013.01); *B01J 31/1805* (2013.01); *B01J 37/0203* (2013.01); *B01J 37/0205* (2013.01); *B01J 37/0213* (2013.01); *C07C 29/157* (2013.01)

(58) Field of Classification Search
None
See application file for complete search history.

(56) References Cited

FOREIGN PATENT DOCUMENTS

| CN | 102397788 A | * | 4/2012 | ............ B01J 24/644 |
|---|---|---|---|---|
| CN | 109317175 | | 2/2019 | |
| CN | 109569686 | | 4/2019 | |

OTHER PUBLICATIONS

Machine-generated English translation of CN 102397788 A (Year: 2012).*

* cited by examiner

*Primary Examiner* — Yun Qian
(74) *Attorney, Agent, or Firm* — JCIP Global Inc.

(57) ABSTRACT

The present invention discloses a selective hydrogenation catalyst and a preparation method and an application thereof, belonging to the technical field of catalysts. The selective hydrogenation catalyst comprises an active component and a carrier for supporting the active component, wherein the active component is a transition metal particle, the carrier is modified by a flexible chain ligand in advance, one end of the flexible chain ligand is uniformly distributed on the surface of the carrier, and the other end of the flexible chain ligand is coordinated on a transition metal. When the catalyst is used for catalytic hydrogenation reaction of dehydrolinalool or 2-methyl-3-butyn-2-ol, the stability is good, the catalyst still has high selectivity after being used for a long time, and the quality of a hydrogenation product can be guaranteed.

2 Claims, 3 Drawing Sheets

SELECTIVE HYDROGENATION CATALYST, PREPARATION METHOD AND APPLICATION THEREOF

CROSS-REFERENCE TO RELATED APPLICATION

This application is a continuation of international PCT application Serial no. PCT/CN2020/081041, filed on Mar. 25, 2020, which claims the priority benefit of China applications no. 202010102438.6, filed on Feb. 19, 2020. The entirety of each of the above-mentioned patent applications is hereby incorporated by reference herein and made a part of this specification.

BACKGROUND

Technical Field

The present invention belongs to the technical field of catalysts, and particularly relates to a selective hydrogenation catalyst and a preparation method and an application thereof.

Description of Related Art

Linalool is a colorless oily liquid with a lily of the valley aroma and belongs to chain terpene alcohols with two isomers, namely α- and β-isomers. Linalool has wide application in the field of fine chemical industry. As an important perfume, it is a blending raw material of various artificial essential oils, and is also widely used for preparing various esters of linalool. Linalool can be oxidized to produce citral, which can also be used to synthesize other perfumes.

With the increasing use of linalool and its derivatives, the development of large-scale industrial green synthesis route is imperative. Scientists have always paid great attention to the synthesis of linalool and its derivatives, and have developed several main synthetic routes in succession. The synthetic route adopted by HOFFMANN LA ROCHE Company in Switzerland is as follows: synthesizing methylheptenone by using acetylene and acetone as raw materials, followed by ethynylation to obtain dehydrolinalool, which is subjected to selective hydrogenation to obtain linalool product. While BASF in Germany uses acetone-isobutylene-formaldehyde method to synthesize methylheptenone, followed by the same ethynylation and selective hydrogenation process to prepare linalool. In summary, the selective hydrogenation of dehydrolinalool plays an important role in the synthesis of linalool.

Selective hydrogenation of dehydrolinalool is an important step in the production of linalool. The over-hydrogenated product, tetrahydrolinalool, has a great impact on the aroma quality of linalool. Therefore, the over-hydrogenation reaction must be effectively inhibited to improve the aroma quality of linalool. Palladium-based catalysts are commonly used industrially to carry out the selective hydrogenation of such alkynols because the transition metal Pd has a good activation property for Hz, and the surface of the transition metal Pd can usually be treated by passivation to suppress the over-hydrogenation reaction, thereby improving the reaction selectivity. The Lindlar catalyst commonly used in the industry adopts this surface passivation strategy, wherein a Pd/CaCO$_3$ catalyst is modified by a combination of additives such as lead and bismuth, and a nitrogen-containing compound or a sulfur-containing compound is added into a reaction system to further inhibit the generation of over-hydrogenation or oligomer. This catalysis strategy has been used in industrial production for decades. However, the application of Lindlar catalyst is greatly limited due to the problems of limited catalyst activity, the existence of toxic additive Pb and insufficient selectivity and the like. In addition, the introduction of auxiliary agents such as quinoline can greatly improve the complexity of the subsequent separation and purification process of the aromatic alcohol. Therefore, it is urgent to develop a more efficient and stable catalyst for selective hydrogenation of alkynols.

Enlightened by Lindlar catalyst, more and more studies show that the metal-organic interface can be formed by surface modification of Pd or Pt catalyst, and the catalytic activity of the catalyst can be improved by adjusting the electronic and spatial structure. Scientists have repeatedly reported that modification of surface organic ligands improves the catalytic performance of transition metal catalysts for selective hydrogenation of acetylenic compounds. For example, the c-Pd/TiS catalyst (Top Catal. 2012, 55, 505-511) developed by BASF using NanoSelect™ technology is a heterogeneous catalyst prepared by modifying Pd nanoparticles with HHDMA and depositing them on a titanium silicate carrier. The use of HHDMA to adjust the electronic and spatial structures of Pd nanoparticles effectively improves the catalytic performance of the catalyst for the selective hydrogenation of acetylenic compounds. However, problems such as the poor stability of the transition metal nanocatalysts modified by similar organic ligands, the unclear molecular mechanism implicit in the catalytic process and the suppressed reaction activity limit the further application of such catalyst systems.

In the Chinese invention patent application CN 109317175A (selective hydrogenation catalyst for alkynol and preparation method and application thereof), nitrogen-containing biomass, a surfactant, an indium-containing metal salt and acid are uniformly mixed and then calcined to obtain a carrier, which is impregnated with a Pd precursor solution, followed by stirring, drying, calcining and reduction with hydrogen, the selective hydrogenation catalyst is obtained. The performance of indium oxide is utilized, and In would preferentially occupy relatively unsaturated Pd sites with lower coordination number to improve the selectivity. However, the carrier is not modified, and metal is directly loaded on the surface of the carrier, causing agglomeration of metal particles, and influencing conversion rate of raw materials and selectivity of products in catalytic hydrogenation. In the Chinese invention patent application CN 109569686A (Preparation of nitrogen-modified carbon-loaded noble metal hydrogenation catalyst and application in halogenated nitrobenzene hydrogenation reaction), activated carbon is pretreated by oxalic acid or hydrogen peroxide to obtain pretreated activated carbon; primary amine organic matters are dissolved in water, added with pretreated activated carbon, fully and uniformly mixed, and then placed in a hydrothermal kettle for a hydrothermal reaction in a CO$_2$ atmosphere to obtain a nitrogen modified activated carbon; and the noble metal palladium or platinum is loaded on the nitrogen modified active carbon by using an ultraviolet light reduction method to obtain the catalyst. The catalyst can be used for the catalytic hydrogenation reaction of halogenated nitrobenzene, and a pyridine nitrogen structure is formed between primary amine and the metal element, influencing the selectivity of the catalyst through the interaction of isomeric electrons. The selectivity of the catalyst of this structure is still low and the stability of the catalyst is poor.

Meanwhile, selective hydrogenation of alkynol is generally carried out in an intermittent reaction kettle, and the method mainly has the following defects: (1) the safety risk is high, hydrogen replacement is needed in the intermittent hydrogenation process, resulting in potential safety hazards in the emptying process; (2) the production efficiency is low, the feeding and discharging operations are complex, and the cycle is long; and (3) the product quality is unstable, each batch of reaction in the intermittent operation is difficult to achieve consistent conditions, and fluctuation of reaction conditions would cause quality fluctuation.

Aiming at the problems, the continuous hydrogenation of the alkynol is carried out in a multi-kettles-in-series mode, not only improving the safety of the reaction and the yield, but also capable of controlling the selectivity of the product through reaction kettle with different volume and catalysts with different mass, guaranteeing the product quality.

SUMMARY

The technical problem to be solved by the present invention is that the selective hydrogenation catalyst in the prior art is low in selectivity and poor in stability, difficult to be used for continuous hydrogenation reaction, and the rapid loss of active components of the catalyst is prone to significantly reduce conversion rate and selectivity of the catalytic hydrogenation reaction, and thus the quality of the hydrogenation product cannot be guaranteed.

In order to solve the above technical problems, the present invention discloses a selective hydrogenation catalyst comprising an active component and a carrier for supporting the active component, wherein the active component is a transition metal particle, and the carrier is modified by a flexible chain ligand in advance, one end of the flexible chain ligand is uniformly distributed on the surface of the carrier, and the other end of the flexible chain ligand is coordinated on the transition metal.

Further, the transition metal particles have an average particle diameter of 0.5-5 nm.

Further, the transition metal particles account for 0.1-10% of the total mass of the catalyst.

The present invention also discloses a method for preparing a selective hydrogenation catalyst, which comprises the following steps:

(1) preparing a carrier, (2) soaking the carrier prepared in the step (1) in a transition metal precursor solution for adsorption treatment; and (3) reducing the adsorbed material obtained in the step (2) to convert the transition metal precursor adsorbed on the surface of the carrier into an elementary substance.

Further, the preparation process of the carrier in the step (1) is as follows: firstly, dispersing a carrier in water, and uniformly mixing to obtain a premix; and then adding a flexible chain ligand into the premix, uniformly mixing, and performing hydrothermal reaction to obtain the flexible chain ligand modified carrier.

Further, the flexible chain ligand is a $C_2$-$C_{30}$ compound having at least one amine group or thiol group at both ends of the molecular chain. Still further, the flexible chain ligands include one or more of ethylenediamine, diethylenetriamine, triethylenetetramine, tetraethylenepentamine, polyethyleneimine, methionine, cysteine, diphenyl sulfide, and 2-fluorophenyl sulfide. Still further, the flexible chain ligands include one or more of diethylenetriamine, triethylenetetramine, tetraethylenepentamine, and diphenyl sulfide.

Further, the carrier is nitrogen-doped multi-stage porous carbon or one or more of oxides of Al, Ti, Zr, Ce, Mo, W, V, Mg, Ca, Mn, Fe, Zn, Ga, Ge, Sn, Y, Nb, La, Re, and Si.

Further, the temperature of the hydrothermal reaction is 50-200° C., and the time of the hydrothermal reaction is 5-20 h. The hydrothermal reaction is carried out to ensure that one end of the flexible chain ligand is bound to the carrier.

Further, the transition metal precursor in the transition metal precursor solution is one or more of $PdCl_2$, $Pd(acac)_2$, $H_2PdCl_4$, $Pd(NO_3)_2$, $Pd(NH_3)_4(NO_3)_2$, $H_2PtCl_6$, $CuCl_2$, $Ni(NO_3)_2$, $IrCl_3$, and $Ir(OAc)_3$.

Further, the reduction method in the step (3) can be hydrogen reduction, formic acid reduction, hydrazine hydrate reduction or sodium borohydride reduction methods. Further, it is hydrogen reduction method. And in the hydrogen reduction process, the temperature is 50-500° C., the heating rate is 1-20° C./min, the time is 1-360 min, and the hydrogen flow rate is 20-200 ml/min.

Further, the molar ratio of the flexible chain ligand to the transition metal content in the transition metal precursor solution is 10-300. This is because the binding of the flexible chain ligand to the transition metal is the binding of multiple flexible chain ligands to a single transition metal, while it is also necessary to ensure that all dispersed flexible chain ligands are bound to the transition metal element.

Further, the amount ratio of the flexible chain ligand to the carrier is 0.1-10 μL/mg.

The selective hydrogenation catalyst prepared by the above method can be used as a catalyst in the selective hydrogenation reaction of alkynol.

Further, the alkynol is dehydrolinalool or 2-methyl-3-butyn-2-ol.

The catalyst is used for the selective hydrogenation process of dehydrolinalool and 2-methyl-3-butyn-2-ol. The catalyst amount is 0.2%-1% of the substrate mass, further, 0.4-0.7%; the reaction temperature is 20-90° C., further, 30-80° C.; and the reaction pressure is 0.5-5 MPa, further, 1-3 MPa. The catalyst can be applied in an intermittent kettle type and continuous kettle type hydrogenation processes, preferably a kettles-in-series mode. The total residence time of the kettles-in-series reaction kettle system is 120-480 min. The catalyst is trapped in the reaction kettle by a filter in an outlet kettle to ensure the constant mass of the catalyst in different kettles. An overflow port of the upper-stage reaction kettle is communicated with a feed port of the next-stage reaction kettle, and the overflow port of the upper-stage reaction is higher than the feed port of the next-stage reaction. The number of reaction kettles in series is 2-4.

According to the present invention, the flexible chain ligand is introduced on the surface of the carrier through hydrothermal reaction to prepare the flexible chain ligand modified composite as the carrier. The flexible chain ligand effectively promotes the dispersion of the transition metal to form highly uniformly dispersed transition metal particles, improving the atom utilization rate of the transition metal, and avoiding the agglomeration of the transition metal in the reduction process. Besides, an amine group or a sulfhydryl group at one end of the flexible chain ligand is coordinated on the surface of the transition metal particle, which directly changing the electronic and spatial structures of the transition metal, and effectively improving the catalytic performance of the catalyst for the selective hydrogenation reaction of alkynol. In addition, due to the interaction of the flexible chain ligand and the transition metal particles, the stability of the transition metal selective hydrogenation catalyst modified by the flexible chain ligand is remarkably improved.

By utilizing the characteristics of the catalyst, the selective hydrogenation process of the alkynol in multi-kettlesin-series mode is realized, and the product quality is greatly improved. Meanwhile, the continuous hydrogenation of the alkynol is carried out in a multi-kettles-in-series mode, not only improving the safety of the reaction and the yield, but also capable of controlling the selectivity of the product through reaction kettles with different volumes and catalysts with different masses, guaranteeing the product quality.

DESCRIPTION OF THE EMBODIMENTS

The technical solutions in the embodiments of the present invention will be described clearly and completely. Obviously, the described embodiments are part of the present invention, but not all of them. Based on the embodiments of the present invention, all other embodiments obtained by a person of ordinary skill in the art without involving any inventive effort are within the scope of the present invention.

The present invention provides a preparation method of a selective hydrogenation catalyst modified by a flexible chain ligand. The preparation method comprises the following steps:

(1) providing a flexible chain ligand modified carrier, wherein the flexible chain ligand is uniformly distributed on the surface of the carrier;

(2) dissolving the carrier modified by the flexible chain ligand in a transition metal precursor solution for adsorption treatment; and (3) reducing the carrier subjected to adsorption treatment, so that the transition metal precursor adsorbed on the surface of the carrier is converted into a transition metal elementary substance, and an amine group or a sulfhydryl group at one end of the flexible chain is coordinated on the active component transition metal.

The preparation method of the flexible chain ligand modified carrier in step (1) specifically comprises the following steps:

Firstly, dissolving the carrier in water, and fully stirring to obtain a premix; then adding the flexible chain ligand to the premix, and subjecting the mixture to a hydrothermal reaction at 50-200° C. to provide the flexible chain ligand modified carrier.

The carrier is nitrogen-doped porous carbon or a metal oxide of one or more elements of Al, Ti, Zr, Ce, Mo, W, V, Mg, Ca, Mn, Fe, Zn, Ga, Ge, Sn, Y, Nb, La and Re.

The premix is a suspension and the carrier is insoluble in the solvent but uniformly distributed in the premix. Stirring is continued for 0.5-2 h during the mixing.

The ratio of the carrier to water is not limited, and further, the ratio of the mass of the carrier to the volume of water is (0.1 g-1 g):30 ml.

The flexible chain ligand is one or more of ethylenediamine, diethylenetriamine, triethylenetetramine, tetraethylenepentamine, polyethyleneimine, methionine, cysteine, diphenyl sulfide, and 2-fluorophenyl sulfide. Further, the flexible chain ligand is one or more of diethylenetriamine, triethylenetetramine, tetraethylenepentamine, diphenyl sulfide.

The reaction time of the hydrothermal reaction is 5-20 h, and further, the reaction time of the hydrothermal reaction is 10-20 h.

It will be appreciated that the hydrothermal reaction products need to be washed and dried prior to the adsorption treatment. The specific treatment process is as follows: filtering the hydrothermal reaction product, washing 3-5 times with a large amount of water and drying at a temperature of 60-100° C. for 6-12 h.

In the step (2), the loading amount (i.e. the mass fraction) of the transition metal in the flexible chain ligand modified selective hydrogenation catalyst can be regulated and controlled, and is not limited; specifically, it can be accomplished by adjusting the mass or molar amount of the transition metal precursor in the transition metal precursor solution.

The method for loading the transition metal on the flexible chain ligand modified carrier comprises the following steps:

dispersing the flexible chain ligand modified carrier in a transition metal precursor solution for adsorption treatment, wherein the adsorption reaction time is 5-15 hours, and further, the adsorption reaction time is 5-10 hours; and reducing the material subjected to adsorption treatment, so that a transition metal precursor adsorbed on flexible chain ligand modified carrier is converted into a transition metal elementary substance, and an amine group or a sulfhydryl group at one end of the flexible chain is coordinated on the active component transition metal.

In the hydrogen reduction process, the temperature is 50-500° C., the heating rate is 1-20° C./min, the time is 1-360 min, and the hydrogen flow rate is 20-200 ml/min.

The transition metal precursor in the transition metal precursor solution is one or more of $PdCl_2$, $Pd(acac)_2$, $H_2PdCl_4$, $Pd(NO_3)_2$, $Pd(NH_3)_4(NO_3)_2$, $H_2PtCl_6$, $CuCl_2$, $Ni(NO_3)_2$, $IrCl_3$, and $Ir(OAc)_3$.

The molar ratio of the fed flexible chain ligand to the transition metal content in the transition metal precursor solution is 10-300.

The present invention also provides a novel flexible chain ligand modified selective hydrogenation catalyst which comprises an active component and a carrier for supporting the active component. The active component is a transition metal particle, the carrier is modified by a flexible chain ligand in advance, and the flexible chain ligand is uniformly distributed on the surface of the composite through hydrothermal reaction. The amine group or the sulfhydryl group at the other end of the flexible chain is directly coordinated on the active component transition metal, changing the electronic and spatial structures of the transition metal, and effectively improving the reaction performance of the flexible chain ligand modified catalyst for the selective hydrogenation reaction of alkynol. Meanwhile, the coordination interaction of the flexible chain ligand and the transition metal particle remarkably improves the stability of the catalyst.

The average particle size of the transition metal particles on the flexible chain ligand modified carrier is 0.5-5 nm. Preferably, the transition metal particles have an average particle size of 0.5-3 nm.

The mass fraction of the transition metal in the catalyst is 0.1-10%.

The present invention also provides an application of the transition metal catalyst modified by the flexible chain ligand in the catalytic hydrogenation reaction. The flexible chain ligand modified transition metal catalyst serves as a catalyst in the selective hydrogenation reaction of alkynol. The alkynol is one of dehydrolinalool and 2-methyl-3-butyn-2-ol. The hydrogenation equations for dehydrolinalool and 2-methyl-3-butyn-2-ol, respectively, are shown below.

The amount of the transition metal in the catalyst is 0.2-1% of the mass of the alkynol.

The selective hydrogenation reaction temperature is 20-90° C., and the reaction pressure is 0.5-5 MPa.

Figure 5:
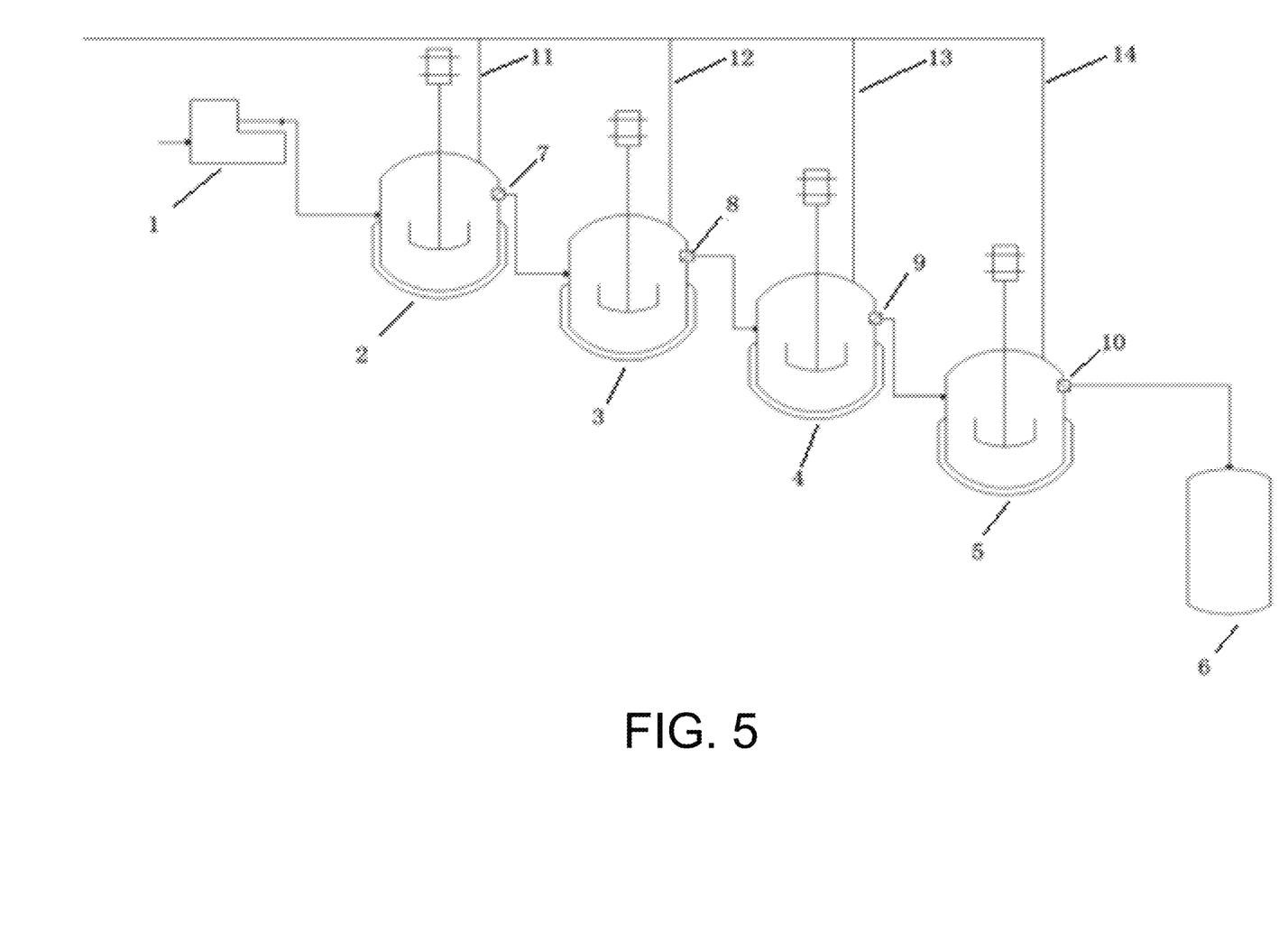
FIG. 5: a diagram of a kettle type continuous hydrogenation device adopted by the present invention.

The total residence time of the multi-kettles-in-series reaction kettle system is 120-480 minutes, the number of the multi-kettles in series is 2-4, and the volume of each reaction kettle can be equal or different. As shown in FIG. 5, a 4-kettles-in-series reaction kettle system is shown: the metering pump 1 is connected with the feeding position of the first reaction kettle 2; in the first to fourth reaction kettles 2-5, the discharge position of the previous reaction kettle is connected with the feed position of the next reaction kettle to form a series connection, wherein the feed position is arranged at the middle side line of the reaction kettle, and the discharge position is arranged at the upper side line of the reaction kettle; the upper ends of the first to fourth reaction kettles 2-5 are provided with air inlets respectively and are connected with the air inlet pipes 11-14 respectively; the discharging positions of the first to fourth reaction kettles 2-5 are respectively provided with overflow ports and filter elements 7-10; and the discharge position of the fourth reaction kettle 5 is connected with a storage tank 6.

The transition metal catalyst modified by flexible chain ligand of the present invention and their application are further illustrated by the following examples.

Example 1

3 g of α-cellulose, 9 g of sodium bicarbonate, 9 g of ammonium oxalate were weighed, stirred thoroughly, transferred to a crucible, and calcined in a nitrogen furnace. The specific calcination process was as follows: maintaining at 30° C. for 30 min, increasing the temperature to 1,000° C. at a rate of 5° C./min, and calcining at 1,000° C. for 2 h; then, naturally lowering the temperature to room temperature. The calcined mixture was fully ground, washed with ultrapure water for three times, and dried at 70° C. overnight to obtain the nitrogen-doped graded porous carbon material.

200 mg of nitrogen-doped graded porous carbon material were weighed, added with 30 ml of ultrapure water, and stirred for 10 minutes. 100 μL of diethylenetriamine was added and stirred for 30 min. Then, hydrothermal reaction was carried out at 150° C. for 10 h. The reaction product was naturally cooled to room temperature, filtered, washed with ultrapure water for three times, and dried at 70° C. overnight to obtain the flexible chain ligand modified nitrogen-doped porous carbon composite, namely the carrier.

150 mg of flexible chain ligand modified nitrogen-doped porous carbon was weighed, added with 20 mL of ultrapure water, and added dropwise with 298 μL of 10 mg/mL $PdCl_2$ solution slowly; the mixture was stirred for adsorption for 5 hours, filtered, washed for three times by using ultrapure water, and dried at 70° C. overnight. Hydrogen reduction was carried out at 300° C. for 2 h, (hydrogen flow rate: 50 mL/min, heating rate: 5° C./min) to obtain the flexible chain ligand modified Pd catalyst.

Figure 1:
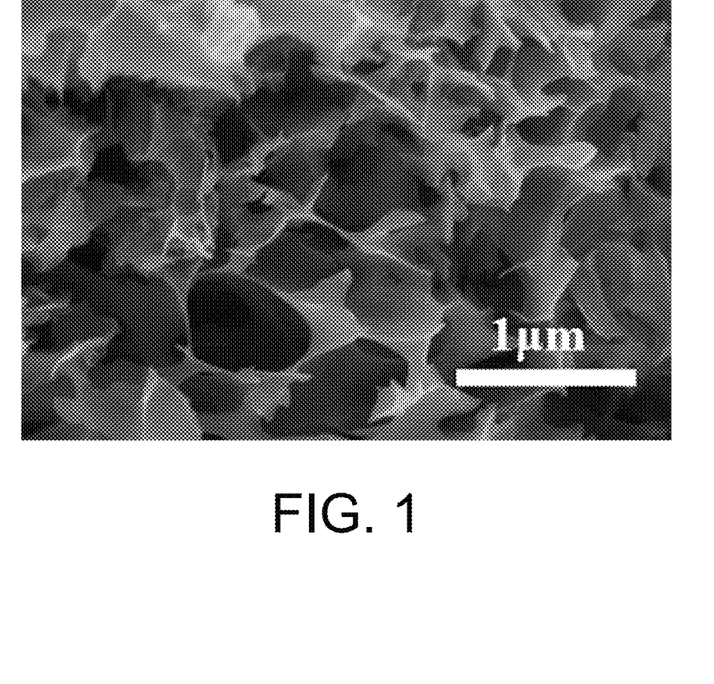
FIG. 1: a scanning electron microscope (SEM) photograph of the flexible chain modified nitrogen-doped porous carbon composite obtained in Example 1.

The nitrogen-doped porous carbon composite was subjected to a scanning electron microscope (SEM) test, and the results are shown in FIG. 1. As can be seen from FIG. 1, a rich pore structure can be clearly observed.

Figure 2:
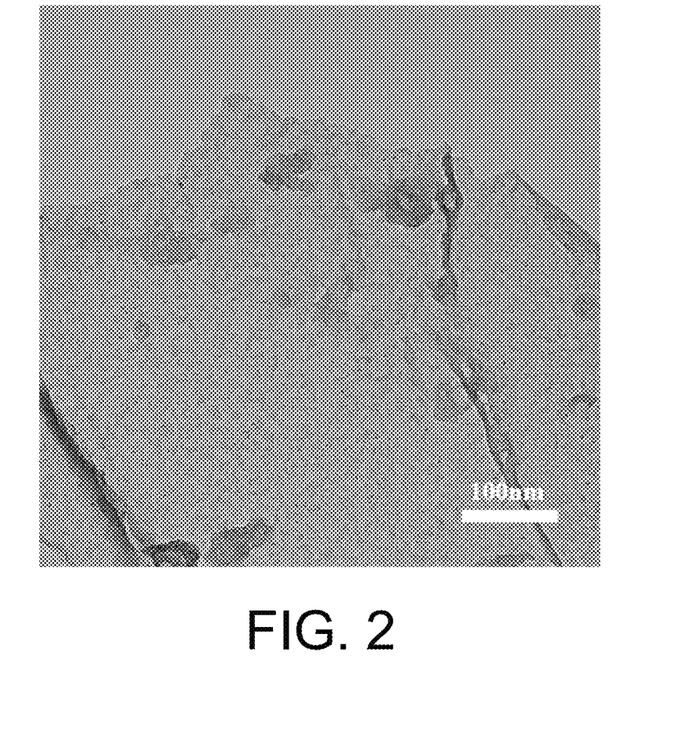
FIG. 2: a transmission electron microscopy (TEM) photograph of the flexible chain ligand modified Pd catalyst described in Example 1.
Figure 3:
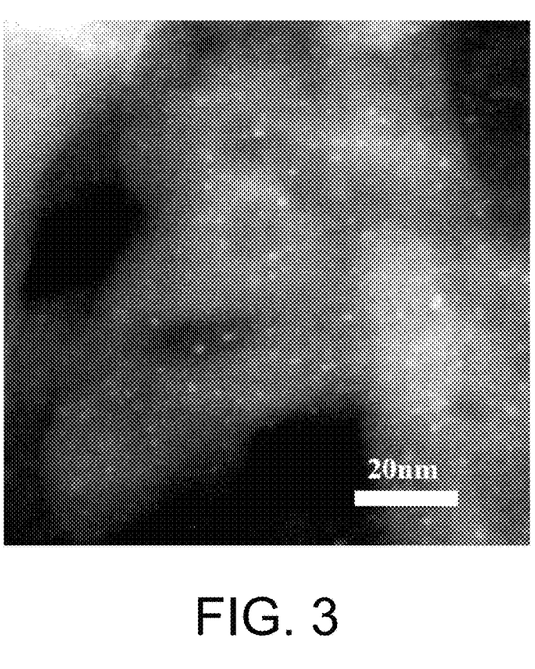
FIG. 3: a dark field scanning transmission electron microscope (STEM) photograph of the flexible chain ligand modified Pd catalyst described in Example 1.

The flexible chain ligand modified Pd catalyst was subjected to transmission electron microscopy (TEM) test and dark field scan transmission electron microscopy (STEM) test, and the results are shown in FIGS. 2 and 3. As can be seen from FIGS. 2 and 3, the Pd particles are uniformly distributed on the surface of the flexible chain ligand modified nitrogen-doped porous carbon carrier.

Figure 4:
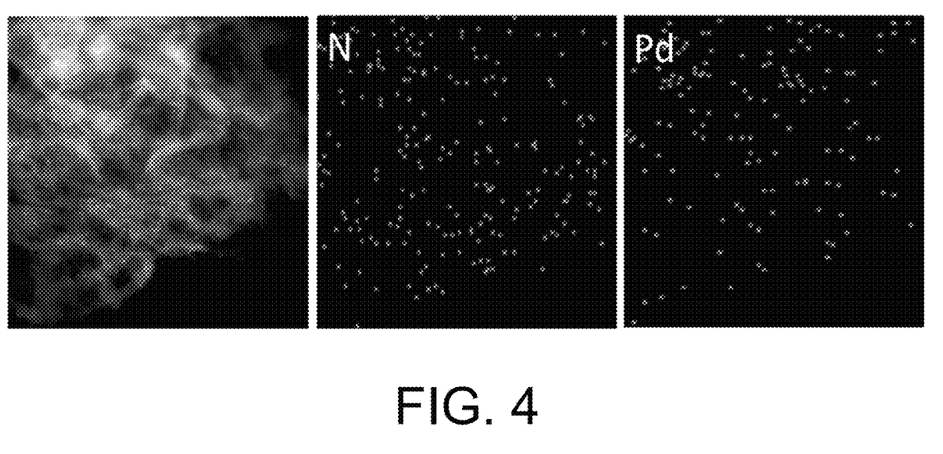
FIG. 4: an x-ray energy dispersive spectrometer (EDS) spectra of the flexible chain ligand modified Pd catalyst described in Example 1.

The flexible chain ligand modified Pd catalyst was subjected to an X-ray energy dispersive spectrometer (EDS) analysis (note: X-ray EDS analysis is an experiment using X-rays to test the distribution state of elements). The result are shown in FIG. 4, and it can be seen that: the Pd element and the N element on the flexible chain ligand modified Pd catalyst are uniformly distributed, and at the same time, as can be seen in the second and third figures in FIG. 4, N and Pd are highly overlapped, thereby proving the effective coordination of the amine group with Pd.

The selective hydrogenation of 2-methyl-3-butyn-2-ol was carried out by two different reaction kettles in series mode. The volume of the first reaction kettle was 10 L, the feed rate was 6 L/h, the catalyst mass was 23.4 g, the reaction temperature was 70° C., and the reaction pressure was 1.5 MPa; and the volume of the second reaction kettle was 50 L, the catalyst mass was 117 g, the reaction temperature was 70° C., the reaction pressure was 1.5 MPa; the total residence time was 420 min, the conversion rate of 2-methyl-3-butyn-2-ol was 99.5%, and the selectivity of 2-methyl-3-buten-2-ol was 98.3%.

Example 2

3 g of α-cellulose, 9 g of sodium bicarbonate, 9 g of ammonium oxalate were weighed, stirred thoroughly, transferred to a crucible, and calcined in a nitrogen furnace. The specific calcination process was as follows: maintaining at 30° C. for 30 min, increasing the temperature to 1,000° C. at a rate of 5° C./min, and calcining at 1,000° C. for 2 h; and then, naturally lowering the temperature to room temperature. The calcined mixture was fully ground, washed with ultrapure water for three times, and dried at 70° C. overnight to obtain the nitrogen-doped porous carbon material.

200 mg of nitrogen-doped porous carbon material were weighed, added with 30 ml of ultrapure water, and stirred for 10 minutes. 20 µL of diethylenetriamine was added and stirred for 30 min. Then, hydrothermally reaction was carried out at 150° C. for 10 h. The reaction product was naturally cooled to room temperature, filtered, washed with ultrapure water for three times, and dried at 70° C. overnight to obtain the flexible chain ligand modified nitrogen-doped porous carbon composite.

150 mg of flexible chain ligand modified nitrogen-doped porous carbon was weighed, added with 20 mL of ultrapure water, and added dropwise with 298 µL of 10 mg/mL PdCl$_2$ solution slowly; the mixture was stirred for adsorption for 5 hours, filtered, washed for three times by using ultrapure water, and dried at 70° C. overnight. Hydrogen reduction was carried out at 300° C. for 2 h, (hydrogen flow rate: 50 mL/min, heating rate: 5° C./min) to obtain the flexible chain ligand modified Pd catalyst.

The flexible chain ligand modified Pd catalyst of Example 2 was prepared in essentially the same manner as in Example 1, except that 20 µL of diethylenetriamine was added during the hydrothermal reaction.

The selective hydrogenation of dehydrolinalool was carried out by two different reaction kettles in series mode. The volume of the first reaction kettle was 10 L, the feed rate was 7 L/h, the catalyst mass was 23.4 g, the reaction temperature was 70° C., and the reaction pressure was 1.0 MPa; the volume of the second reaction kettle was 50 L, the catalyst mass was 117 g, the reaction temperature was 70° C., the reaction pressure was 1.0 MPa; the total residence time was 360 min, the conversion rate of dehydrolinalool was 99%, and the selectivity of dehydrolinalool was 98.0%.

Example 3

3 g of α-cellulose, 9 g of sodium bicarbonate, 9 g of ammonium oxalate were weighed, stirred thoroughly, transferred to a crucible, and calcined in a nitrogen furnace. The specific calcination process was as follows: maintaining at 30° C. for 30 min, increasing the temperature to 1,000° C. at a rate of 5° C./min, and calcining at 1,000° C. for 2 h; and then, naturally lowering the temperature to room temperature. The calcined mixture was fully ground, washed with ultrapure water for three times, and dried at 70° C. overnight to obtain the nitrogen-doped porous carbon material.

200 mg of nitrogen-doped graded porous carbon material were weighed, added with 30 ml of ultrapure water, and stirred for 10 minutes. 40 µL of diethylenetriamine was added and stirred for 30 min. Then, hydrothermally reaction was carried out at 150° C. for 10 h. The reaction product was naturally cooled to room temperature, filtered, washed with ultrapure water for three times, and dried at 70° C. overnight to obtain the flexible chain ligand modified nitrogen-doped porous carbon composite.

150 mg of flexible chain ligand modified nitrogen-doped porous carbon was weighed, added with 20 mL of ultrapure water, and added dropwise with 298 µL of 10 mg/mL PdCl$_2$ solution slowly; the mixture was stirred for adsorption for 5 h, filtered, washed for three times by using ultrapure water, and dried at 70° C. overnight. Hydrogen reduction was carried out at 300° C. for 2 h, (hydrogen flow rate: 50 mL/min, heating rate: 5° C./min) to obtain the flexible chain ligand modified Pd catalyst.

The flexible chain ligand modified Pd catalyst of Example 3 was prepared in essentially the same manner as in Example 1, except that 40 µL of diethylenetriamine was added during the hydrothermal reaction.

The selective hydrogenation of 2-methyl-3-butyn-2-ol was carried out by a four different reaction kettles in series mode. The volume of the first reaction kettle was 10 L, the feed rate was 6 L/h, the catalyst mass was 23.4 g, the reaction temperature was 80° C., and the reaction pressure was 2 MPa; the volume of the second reaction kettle was 10 L, the catalyst mass was 23.4 g, the reaction temperature was 80° C., and the reaction pressure was 2 MPa; the volume of the third reaction kettle was 10 L, the catalyst mass was 23.4 g, the reaction temperature was 80° C., and the reaction pressure was 2 MPa; the volume of the fourth reaction kettle was 10 L, the catalyst mass was 23.4 g, the reaction temperature was 80° C., the reaction pressure was 2 MPa; the total residence time was 280 min, the conversion rate of 2-methyl-3-butyn-2-ol was 99.5%, and the selectivity of 2-methyl-3-butyn-2-ol was 98.2%.

Example 4

200 mg of commercial alumina material was weighed, added with 30 ml of ultrapure water, and stirred for 10 min. 100 µL of diethylenetriamine was added and stirred for 30 min. Then, hydrothermally reaction was carried out at 150° C. for 10 h. The reaction product was naturally cooled to room temperature, filtered, washed with ultrapure water for three times, and dried at 70° C. overnight to obtain the flexible chain ligand modified alumina composite.

150 mg of flexible chain ligand modified alumina was weighed, added with 20 mL of ultrapure water, and added dropwise with 298 µL of 10 mg/mL PdCl$_2$ solution slowly; the mixture was stirred for adsorption for 5 hours, filtered, washed for three times by using ultrapure water, and dried at 70° C. overnight. Hydrogen reduction was carried out at 300° C. for 2 h, (hydrogen flow rate: 50 mL/min, heating rate: 5° C./min) to obtain the flexible chain ligand modified Pd catalyst.

The flexible chain ligand modified Pd catalyst of Example 4 was prepared in essentially the same manner as in Example 1, except that the carrier was commercial alumina.

The selective hydrogenation of dehydrolinalool was carried out by two different reaction kettles in series mode. The volume of the first reaction kettle was 10 L, the feed rate was 7 L/h, the catalyst mass was 23.4 g, the reaction temperature was 80° C., and the reaction pressure was 1.0 MPa; and the volume of the second reaction kettle was 50 L, the catalyst mass was 117 g, the reaction temperature was 80° C., the reaction pressure was 1.0 MPa; the total residence time was 360 min, the conversion rate of dehydrolinalool was 99.4%, and the selectivity of dehydrolinalool was 97.6%.

Example 5

The flexible chain ligand modified Pd catalyst of Example 5 was prepared in essentially the same manner as in Example 1, except that 100 µL of ethylenediamine was added during the hydrothermal reaction.

The selective hydrogenation of dehydrolinalool was carried out by two different reaction kettles in series mode. The volume of the first reaction kettle was 10 L, the feed rate was 7 L/h, the catalyst mass was 46.8 g, the reaction temperature was 75° C., and the reaction pressure was 1.0 MPa; the volume of the second reaction kettle was 50 L, the catalyst mass was 175 g, the reaction temperature was 75° C., the reaction pressure was 1.0 MPa; the total residence time was 360 min, the conversion rate of dehydrolinalool was 99.6%, and the selectivity of dehydrolinalool was 98.1%.

Example 6

The flexible chain ligand modified Pd catalyst of Example 6 was prepared in essentially the same manner as in Example 1, except that 100 μL of triethylenetetramine was added during the hydrothermal reaction.

The selective hydrogenation of 2-methyl-3-butyn-2-ol was carried out by four different reaction kettles in series mode. The volume of the first reaction kettle was 10 L, the feed rate was 6 L/h, the catalyst mass was 46.8 g, the reaction temperature was 70° C., and the reaction pressure was 2 MPa; the volume of the second reaction kettle was 10 L, the catalyst mass was 23.4 g, the reaction temperature was 70° C., and the reaction pressure was 2 MPa; the volume of the third reaction kettle was 10 L, the catalyst mass was 23.4 g, the reaction temperature was 70° C., and the reaction pressure was 2 MPa; the volume of the fourth reaction kettle was 10 L, the catalyst mass was 23.4 g, the reaction temperature was 70° C., the reaction pressure was 2 MPa; the total residence time was 280 min, the conversion rate of 2-methyl-3-butyn-2-ol was 99.5%, and the selectivity of 2-methyl-3-butyn-2-ol was 98.1%.

Example 7

The flexible chain ligand modified Pd catalyst of Example 7 was prepared in essentially the same manner as in Example 1, except that 100 μL of diphenyl sulfide was added during the hydrothermal reaction.

The selective hydrogenation of dehydrolinalool was carried out by two different reaction kettles in series mode. The volume of the first reaction kettle was 10 L, the feed rate was 7 L/h, the catalyst mass was 46.8 g, the reaction temperature was 75° C., and the reaction pressure was 1.0 MPa; and the volume of the second reaction kettle was 50 L, the catalyst mass was 175 g, the reaction temperature was 75° C., the reaction pressure was 1.0 MPa; the total residence time was 360 min, the conversion rate of dehydrolinalool was 99.6%, and the selectivity of dehydrolinalool was 98.1%.

Comparative Example 1

The selective hydrogenation catalyst was prepared essentially the same as in Example 1 except that no flexible chain ligand was added and no hydrothermal reaction was performed.

The selective hydrogenation of 2-methyl-3-butyn-2-ol was carried out by two different reaction kettles in series mode. The volume of the first reaction kettle was 10 L, the feed rate was 7 L/h, the catalyst mass was 23.4 g, the reaction temperature was 70° C., and the reaction pressure was 1.0 MPa; and the volume of the second reaction kettle was 50 L, the catalyst mass was 117 g, the reaction temperature was 70° C., the reaction pressure was 1.0 MPa; the total residence time was 360 min, the conversion rate of 2-methyl-3-butyn-2-ol was 70.4%, and the selectivity of 2-methyl-3-buten-2-ol was 32.5%.

Comparative Example 2

The selective hydrogenation catalyst was prepared essentially the same as in Example 1 except that no flexible chain ligand was added and no hydrothermal reaction was performed.

The selective hydrogenation of dehydrolinalool was carried out by two different reaction kettles in series mode. The volume of the first reaction kettle was 10 L, the feed rate was 7 L/h, the catalyst mass was 23.4 g, the reaction temperature was 70° C., and the reaction pressure was 1.0 MPa; the volume of the second reaction kettle was 50 L, the catalyst mass was 117 g, the reaction temperature was 70° C., the reaction pressure was 1.0 MPa; the total residence time was 360 min, the conversion rate of dehydrolinalool was 65.7%, and the selectivity of dehydrolinalool was 43.5%.

Comparative Example 3

The selective hydrogenation catalyst was prepared essentially the same as in Example 1 except 167 mg of o-phenanthroline was added during the hydrothermal reaction.

The selective hydrogenation of 2-methyl-3-butyn-2-ol was carried out by two different reaction kettles in series mode. The volume of the first reaction kettle was 10 L, the feed rate was 6 L/h, the catalyst mass was 23.4 g, the reaction temperature was 70° C., and the reaction pressure was 1.5 MPa; and the volume of the second reaction kettle was 50 L, the catalyst mass was 117 g, the reaction temperature was 70° C., the reaction pressure was 1.5 MPa; the total residence time was 420 min, the conversion rate of 2-methyl-3-butyn-2-ol was 46.8%, and the selectivity of 2-methyl-3-buten-2-ol was 75.4%.

Comparative Example 4

The selective hydrogenation catalyst was prepared essentially the same as in Example 1 except 167 mg of o-phenanthroline was added during the hydrothermal reaction.

The selective hydrogenation of dehydrolinalool was carried out by two different reaction kettles in series mode. The volume of the first reaction kettle was 10 L, the feed rate was 6 L/h, the catalyst mass was 23.4 g, the reaction temperature was 70° C., and the reaction pressure was 1.5 MPa; the volume of the second reaction kettle was 50 L, the catalyst mass was 117 g, the reaction temperature was 70° C., the reaction pressure was 1.5 MPa; the total residence time was 420 min, the conversion rate of dehydrolinalool was 38.5%, and the selectivity of dehydrolinalool was 77.0%.

The actual loading amounts of the transition metals in the catalysts obtained in the above Examples 1 to 7 and Comparative Examples 1 to 4 were measured by the atomic emission spectroscopy.

Table 1 below shows the raw materials, partial process parameters and catalytic hydrogenation effects of the selective hydrogenation catalysts used in Examples 1-7 and Comparative Examples 1-4 above.

TABLE 1 raw materials, partial process parameters and catalytic hydrogenation effects of the selective hydrogenation catalysts used in each example and comparative example.

| Nos | Flexible chain ligands | Molar ratio of flexible chain ligand to transition metal content in transition metal precursor solution | Amount ratio of flexible chain ligand to carrier, μL/mg | Partial process parameters | Transition metal loading amount | Catalytic hydrogenation effects Raw material conversion rates | Selectivity |
|---|---|---|---|---|---|---|---|
| Example 1 | Diethylenetriamine, 100 μL | 55.30 | 0.5 | Hydrothermal reaction temperature: 150° C. Hydrothermal reaction time: 10 h | 0.79% | 2-Methyl-3-butyn-2-ol, 99.5% | 98.3% |
| Example 2 | Diethylenetriamine, 20 μL | 11.06 | 0.1 | Hydrothermal reaction temperature: 150° C. Hydrothermal reaction time: 10 h | 0.81% | Dehydrolinalool, 99% | 98.0% |
| Example 3 | Diethylenetriamine, 40 μL | 22.12 | 0.2 | Hydrothermal reaction temperature: 150° C. Hydrothermal reaction time: 10 h | 0.8% | 2-Methyl-3-butyn-2-ol, 99.5% | 98.2% |
| Example 4 | Diethylenetriamine, 100 μL Carrier: commercial alumina | 55.30 | 0.5 | Hydrothermal reaction temperature: 150° C. Hydrothermal reaction time: 10 h | 0.8% | Dehydrolinalool, 99.4% | 97.6% |
| Example 5 | Ethylenediamine, 100 μL | 89.17 | 0.5 | Hydrothermal reaction temperature: 150° C. Hydrothermal reaction time: 10 h | 0.78% | Dehydrolinalool, 99.6% | 98.1% |
| Example 6 | Triethylenetetramine, 100 μL | 39.94 | 0.5 | Hydrothermal reaction temperature: 150° C. Hydrothermal reaction time: 10 h | 0.74% | 2-Methyl-3-butyn-2-ol, 99.5% | 98.1% |
| Example 7 | Diphenyl sulfide, 100 μL | 35.59 | 0.5 | Hydrothermal reaction temperature: 150° C. Hydrothermal reaction time: 10 h | 0.82% | Dehydrolinalool, 99.6% | 98.1% |
| Comparative Example 1 | — | — | — | — | 0.84% | 2-methyl-3-butyn-2-ol, 70.4% | 32.5% |
| Comparative Example 2 | — | — | — | — | 0.84% | Dehydrolinalool, 65.7% | 43.5% |
| Comparative Example 3 | O-Phenanthroline 167 mg | 55.30 | — | Hydrothermal reaction temperature: 150° C. Hydrothermal reaction time: 10 h | 0.75% | 2-methyl-3-butyn-2-ol, 46.8% | 75.4% |
| Comparative Example 4 | O-Phenanthroline 167 mg | 55.30 | — | Hydrothermal reaction temperature: 150° C. Hydrothermal reaction time: 10 h | 0.75% | Dehydrolinalool, 38.5% | 77.0% |

As can be seen from the data in Table 1 above, Examples 1-7 using the selective hydrogenation catalyst obtained by the preparation method of the present invention have higher conversions and selectivity in the catalytic hydrogenation of dehydrolinalool and 2-methyl-3-butyn-2-ol than Comparative Examples 1-4 without the catalyst obtained by the preparation method of the present invention.

Meanwhile, in order to verify that the selective hydrogenation catalyst obtained by the preparation method of the present invention can maintain high conversion rates and selectivity, i.e., has high stability, in a continuous hydrogenation reaction, the following examples and comparative examples were designed.

Examples 8-9, Comparative Examples 5-6

According to the method for selectively hydrogenating of 2-methyl-3-butyn-2-ol in Example 1, stability experiment comparison was carried out using the catalysts obtained in Example 1 and Comparative Example 1, respectively, and the results are shown in Table 2 below:

TABLE 2

Conversion rates and selectivity of different selective hydrogenation catalysts after continuous hydrogenation of 2-methyl-3-butyn-2-ol

| Nos | Sources of catalyst | Continuous reaction time, h | Conversion rates, % | Selectivity, % |
|---|---|---|---|---|
| Example 8 | Example 1 | 50 | 99.6 | 98.2 |
| Example 9 | Example 1 | 100 | 98.4 | 98.3 |
| Comparative Example 5 | Comparative Example 1 | 50 | 60.2 | 30.2 |
| Comparative Example 6 | Comparative Example 1 | 100 | 44.6 | 28.4 |

Examples 10-11, Comparative Examples 7-8

According to the method for selectively hydrogenating of dehydrolinalool in Example 2, stability experiment comparison was carried out using the catalysts obtained in Example 1 and Comparative Example 1, respectively, and the results are shown in Table 3 below:

TABLE 3

Conversion rates and selectivity of different selective hydrogenation catalysts after continuous hydrogenation of dehydrolinalool

| Nos | Sources of catalyst | Continuous reaction time, h | Conversion rates, % | Selectivity, % |
|---|---|---|---|---|
| Example 10 | Example 1 | 50 | 99.4 | 98.5 |
| Example 11 | Example 1 | 100 | 98.7 | 98.2 |
| Comparative Example 7 | Comparative Example 1 | 50 | 45.7 | 58.4 |
| Comparative Example 8 | Comparative Example 1 | 100 | 30.2 | 40.2 |

As can be seen from the above Tables 2 and 3, the reduction in conversion rate of Examples 8-9 and Examples 10-11 relative to Comparative Examples 5-6 and 7-8, respectively, indicates a certain loss of catalyst, while the catalyst of the present invention still maintain the conversion rate of more than 98% after continuously reacting for 100 h in the continuous hydrogenation reaction of 2-methyl-3-butyn-2-ol and dehydrolinalool, respectively. The loss rate is low, and after the selective hydrogenation catalyst is used for 100 hours of catalytic hydrogenation reaction. Although the active components of the catalyst are lost to a certain extent, the catalytic hydrogenation reaction still has higher selectivity of more than 98%, and the hydrogenation product can still be guaranteed to have higher quality, so that the selective hydrogenation catalyst obtained by the present invention has better stability.

The embodiments described above represent only a few embodiments of the present invention, the description of which is specific and detailed, but should not be construed to limit the scope of the present invention. It should be noted that several variations and modifications may be made by those skilled in the art without departing from the spirit of the present invention, which fall within the scope of the present invention. Therefore, the scope of the patent for invention shall be determined by the appended claims.

What is claimed is:

1. An application of a selective hydrogenation catalyst in a catalytic hydrogenation reaction, characterized in that the selective hydrogenation catalyst serves as a catalyst in the selective hydrogenation reaction of alkynol, wherein a step of the catalytic hydrogenation reaction includes:

feeding the selective hydrogenation catalyst, the alkynol, and hydrogen in a reaction kettle, wherein the selective hydrogenation catalyst is obtained by comprising:

step (1) dispersing a carrier in water and uniformly mixing to obtain a premix, adding and uniformly mixing a flexible chain ligand into the premix, and performing a hydrothermal reaction to obtain a flexible chain ligand modified carrier;

step (2) soaking the carrier prepared in the step (1) in a transition metal precursor solution for an adsorption treatment to obtain an adsorbed material; and step (3) reducing the adsorbed material obtained in the step (2) to convert a transition metal precursor adsorbed on the surface of the carrier into a transition metal elementary substance, wherein a molar ratio of the flexible chain ligand to a transition metal content in the transition metal precursor solution is 10-300, wherein an amount ratio of the flexible chain ligand to the carrier is 0.1-10 μL/mg, wherein a temperature of the hydrothermal reaction is 50-200° C. and a time of the hydrothermal reaction is 5-20 hours, wherein one end of the flexible chain ligand is uniformly distributed on the surface of the carrier, and the other end of the flexible chain ligand is coordinated on the transition metal; and the selective hydrogenation reaction of the alkynol is performed in the reaction kettle through the selective hydrogenation catalyst to form a hydrogenation product, wherein a temperature of the selective hydrogenation reaction is 20-90° C., and a pressure of the selective hydrogenation reaction is 0.5-5 MPa, wherein the flexible chain ligand comprises one or more of ethylenediamine, diethylenetriamine, and triethylenetetramine, wherein the carrier is nitrogen-doped multi-stage porous carbon, wherein the transition metal precursor in the transition metal precursor solution comprises $PdCl_2$.

2. The application of claim 1, characterized in that the alkynol is dehydrolinalool or 2-methyl-3-butyn-2-ol.

* * * * *